US007751892B2

(12) United States Patent
Peterson et al.

(10) Patent No.: US 7,751,892 B2
(45) Date of Patent: Jul. 6, 2010

(54) IMPLANTABLE MEDICAL DEVICE PROGRAMMING APPARATUS HAVING A GRAPHICAL USER INTERFACE

(75) Inventors: Les Norman Peterson, Woodbury, MN (US); Paula Dieterle, Champlin, MN (US); LanAnh Nguyen, Plymouth, MN (US); James Kalgren, Lino Lakes, MN (US); James O. Gilkerson, Stillwater, MN (US); Dorothy Marie Nauman, Stillwater, MN (US); Aaron Raymond Peterson, Ham Lake, MN (US); Mark Joseph Schwartz, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/841,967

(22) Filed: May 6, 2004

(65) Prior Publication Data

US 2005/0033385 A1 Feb. 10, 2005

Related U.S. Application Data

(60) Provisional application No. 60/468,902, filed on May 7, 2003.

(51) Int. Cl.
*A61N 1/362* (2006.01)

(52) U.S. Cl. ..................................................... 607/30
(58) Field of Classification Search ............. 607/30–32, 607/59, 60
See application file for complete search history.

(56) References Cited

U.S. PATENT DOCUMENTS 4,006,737 A    2/1977   Cherry 4,090,505 A    5/1978   Mortara
4,163,451 A    8/1979   Lesnick et al.
4,166,470 A    9/1979   Neumann
4,172,459 A   10/1979   Hepp
4,187,854 A    2/1980   Hepp et al.

(Continued)

FOREIGN PATENT DOCUMENTS

EP    0491649 A2    6/1992

(Continued)

OTHER PUBLICATIONS

*Vigor Model 2950 Physician's System Manual*, Cardiac Pacemakers, Inc., St. Paul, MN, (1996), 87 pgs.

(Continued)

*Primary Examiner*—George R Evanisko
(74) *Attorney, Agent, or Firm*—Schwegman, Lundberg & Woessner, P.A.

(57) ABSTRACT

Systems and methods for a configurable programmer for an implantable cardiovascular medical device are disclosed. A preferred embodiment comprises a graphical user interface to visualize programming processes to alert a clinician to potential problems with the patient's condition or the therapy provided by the device, or the device itself. The programmer is further adapted to minimize the risk of programming potentially dangerous changes to the implantable device's parameter settings by requiring the clinician to first review new value changes before initiating the programming step. The programmer also allows the clinician to view how a change to one or more parameter settings affect other settings before the implantable device is programmed or re-programmed.

22 Claims, 15 Drawing Sheets

U.S. PATENT DOCUMENTS

| | | |
|---|---|---|
| 4,197,850 A | 4/1980 | Schulman et al. |
| 4,232,679 A | 11/1980 | Schulman |
| 4,236,524 A | 12/1980 | Powell et al. |
| 4,316,249 A | 2/1982 | Gallant et al. |
| 4,336,810 A | 6/1982 | Anderson et al. |
| 4,407,288 A | 10/1983 | Langer et al. |
| 4,503,857 A | 3/1985 | Boute et al. |
| 4,509,530 A | 4/1985 | Curtis et al. |
| 4,529,401 A | 7/1985 | Leslie et al. |
| 4,549,552 A | 10/1985 | Groch et al. |
| 4,562,841 A | 1/1986 | Brockway et al. |
| 4,680,708 A | 7/1987 | Ambos et al. |
| 4,800,883 A | 1/1989 | Winstrom |
| 4,809,697 A | 3/1989 | Causey, III et al. |
| 4,825,869 A | 5/1989 | Sasmor et al. |
| 4,830,006 A | 5/1989 | Haluska et al. |
| 4,850,357 A | 7/1989 | Bach, Jr. |
| 4,944,298 A | 7/1990 | Sholder |
| 4,947,857 A | 8/1990 | Albert et al. |
| 4,958,632 A | 9/1990 | Duggan |
| 4,964,410 A | 10/1990 | Leahey et al. |
| 4,974,598 A | 12/1990 | John |
| 4,989,610 A | 2/1991 | Patton et al. |
| 4,998,531 A | 3/1991 | Bocchi et al. |
| 5,000,189 A | 3/1991 | Throne et al. |
| 5,012,814 A | 5/1991 | Mills et al. |
| 5,027,824 A | 7/1991 | Dougherty et al. |
| 5,046,504 A | 9/1991 | Albert et al. |
| 5,047,930 A | 9/1991 | Martens et al. |
| 5,050,612 A | 9/1991 | Matsumura |
| 5,052,395 A | 10/1991 | Burton et al. |
| 5,085,215 A | 2/1992 | Nappholz et al. |
| 5,111,816 A | 5/1992 | Pless et al. |
| 5,113,869 A | 5/1992 | Nappholz et al. |
| 5,129,392 A | 7/1992 | Bardy et al. |
| 5,144,949 A | 9/1992 | Olson |
| 5,156,147 A | 10/1992 | Warren et al. |
| 5,184,614 A | 2/1993 | Collins et al. |
| 5,193,550 A | 3/1993 | Duffin |
| 5,197,467 A | 3/1993 | Steinhaus et al. |
| 5,215,083 A | 6/1993 | Drane et al. |
| 5,217,021 A | 6/1993 | Steinhaus et al. |
| 5,224,475 A | 7/1993 | Berg et al. |
| 5,273,049 A | 12/1993 | Steinhaus et al. |
| 5,279,293 A | 1/1994 | Andersen et al. |
| 5,292,339 A | 3/1994 | Stephens et al. |
| 5,292,341 A * | 3/1994 | Snell ........................... 607/30 |
| 5,299,118 A | 3/1994 | Martens et al. |
| 5,309,919 A * | 5/1994 | Snell et al. ................... 600/510 |
| 5,311,873 A | 5/1994 | Savard et al. |
| 5,311,874 A | 5/1994 | Baumann et al. |
| 5,312,441 A | 5/1994 | Mader et al. |
| 5,315,512 A | 5/1994 | Roth |
| 5,341,811 A | 8/1994 | Cano |
| 5,342,402 A | 8/1994 | Olson et al. |
| 5,344,430 A | 9/1994 | Berg et al. |
| 5,404,877 A | 4/1995 | Nolan et al. |
| 5,411,530 A | 5/1995 | Akhtar |
| 5,421,830 A * | 6/1995 | Epstein et al. ................ 607/30 |
| 5,423,871 A | 6/1995 | Hoegnelid et al. |
| 5,458,623 A | 10/1995 | Lu et al. |
| 5,464,433 A | 11/1995 | White et al. |
| 5,480,413 A | 1/1996 | Greenhut et al. |
| 5,487,754 A | 1/1996 | Snell et al. |
| 5,487,755 A | 1/1996 | Snell et al. |
| 5,496,351 A | 3/1996 | Plicchi et al. |
| 5,513,645 A | 5/1996 | Jacobson et al. |
| 5,535,753 A | 7/1996 | Petrucelli et al. |
| 5,549,646 A | 8/1996 | Katz et al. |
| 5,549,649 A | 8/1996 | Florio et al. |
| 5,549,654 A | 8/1996 | Powell |
| 5,555,888 A | 9/1996 | Brewer et al. |
| 5,578,063 A | 11/1996 | Bocek et al. |
| 5,584,298 A | 12/1996 | Kabal |
| 5,584,867 A | 12/1996 | Limousin et al. |
| 5,603,331 A | 2/1997 | Heemels et al. |
| 5,607,460 A | 3/1997 | Kroll et al. |
| 5,609,612 A | 3/1997 | Plicchi et al. |
| 5,613,495 A | 3/1997 | Mills et al. |
| 5,620,474 A | 4/1997 | Koppman |
| 5,626,620 A | 5/1997 | Kieval et al. |
| 5,626,623 A | 5/1997 | Kieval et al. |
| 5,628,321 A | 5/1997 | Scheib et al. |
| 5,643,255 A | 7/1997 | Organ |
| 5,647,369 A | 7/1997 | Petrucelli et al. |
| 5,674,249 A | 10/1997 | De Coriolis et al. |
| 5,683,431 A | 11/1997 | Wang |
| 5,687,737 A | 11/1997 | Branham et al. |
| 5,693,075 A | 12/1997 | Plicchi et al. |
| 5,697,959 A | 12/1997 | Poore |
| 5,713,366 A | 2/1998 | Armstrong et al. |
| 5,713,929 A | 2/1998 | Hess et al. |
| 5,716,383 A | 2/1998 | Kieval et al. |
| 5,716,384 A | 2/1998 | Snell |
| 5,722,999 A | 3/1998 | Snell |
| 5,724,985 A * | 3/1998 | Snell et al. ................... 600/510 |
| 5,725,561 A | 3/1998 | Stroebel et al. |
| 5,743,268 A | 4/1998 | Kabal |
| 5,749,900 A | 5/1998 | Schroeppel et al. |
| 5,749,906 A | 5/1998 | Kieval et al. |
| 5,749,907 A | 5/1998 | Mann |
| 5,749,908 A | 5/1998 | Snell |
| 5,755,742 A | 5/1998 | Schuelke et al. |
| 5,759,199 A | 6/1998 | Snell et al. |
| 5,772,604 A | 6/1998 | Langberg et al. |
| 5,785,660 A | 7/1998 | van Lake et al. |
| 5,788,640 A | 8/1998 | Peters |
| 5,792,203 A | 8/1998 | Schroeppel |
| 5,792,204 A | 8/1998 | Snell |
| 5,814,088 A | 9/1998 | Paul et al. |
| 5,817,137 A | 10/1998 | Kaemmerer |
| 5,818,137 A | 10/1998 | Kaemmerer |
| 5,833,623 A | 11/1998 | Mann et al. |
| 5,876,353 A | 3/1999 | Riff |
| 5,891,043 A | 4/1999 | Ericksen et al. |
| 5,891,178 A | 4/1999 | Mann et al. |
| 5,891,179 A | 4/1999 | Er et al. |
| 5,897,577 A | 4/1999 | Cinbis et al. |
| 5,924,989 A | 7/1999 | Polz |
| 5,948,005 A | 9/1999 | Valikai et al. |
| 5,951,484 A | 9/1999 | Hoium et al. |
| 5,954,664 A | 9/1999 | Seegobin |
| 5,957,861 A | 9/1999 | Combs et al. |
| 5,961,467 A | 10/1999 | Shimazu et al. |
| 5,974,341 A | 10/1999 | Er et al. |
| 5,978,707 A | 11/1999 | Krig et al. |
| 6,004,276 A | 12/1999 | Wright et al. |
| 6,007,493 A | 12/1999 | Ericksen et al. |
| 6,016,442 A | 1/2000 | Hsu et al. |
| 6,016,447 A | 1/2000 | Juran et al. |
| 6,016,448 A | 1/2000 | Busacker et al. |
| 6,017,307 A | 1/2000 | Raines |
| 6,035,233 A | 3/2000 | Schroeppel et al. |
| 6,091,990 A | 7/2000 | Hsu et al. |
| 6,101,415 A | 8/2000 | Er et al. |
| 6,151,524 A | 11/2000 | Krig et al. |
| 6,223,072 B1 | 4/2001 | Mika et al. |
| 6,240,317 B1 | 5/2001 | Villaseca et al. |
| 6,253,102 B1 | 6/2001 | Hsu et al. |
| 6,289,244 B1 | 9/2001 | Conley et al. |
| 6,289,248 B1 | 9/2001 | Conley et al. |
| 6,301,503 B1 * | 10/2001 | Hsu et al. ..................... 607/30 |
| 6,304,778 B1 | 10/2001 | Gilkerson et al. |
| 6,317,632 B1 | 11/2001 | Krig et al. |

| | | | |
|---|---|---|---|
| 6,370,432 | B1 | 4/2002 | Conley et al. |
| 6,381,494 | B1 | 4/2002 | Gilkerson et al. |
| 6,415,175 | B1 * | 7/2002 | Conley et al. ............... 600/523 |
| 6,430,439 | B1 | 8/2002 | Wentkowski et al. |
| 6,438,421 | B1 | 8/2002 | Stahmann et al. |
| 6,449,504 | B1 | 9/2002 | Conley et al. |
| 6,480,742 | B2 | 11/2002 | Stahmann et al. |
| 6,493,579 | B1 | 12/2002 | Gilkerson et al. |
| 6,522,925 | B1 * | 2/2003 | Gilkerson et al. ............. 607/30 |
| 6,526,314 | B1 | 2/2003 | Eberle et al. |
| 6,535,763 | B1 | 3/2003 | Hiebert et al. |
| 6,553,258 | B2 | 4/2003 | Stahmann et al. |
| 6,618,618 | B2 | 9/2003 | Kalgren et al. |
| 6,644,322 | B2 | 11/2003 | Webb |
| 6,665,558 | B2 | 12/2003 | Kalgren et al. |
| 6,678,560 | B1 | 1/2004 | Gilkerson et al. |
| 6,687,539 | B2 | 3/2004 | Gilkerson et al. |
| 6,795,734 | B2 | 9/2004 | Vanderlinde et al. |
| 6,823,210 | B2 | 11/2004 | Eberle et al. |
| 6,842,644 | B2 | 1/2005 | Anderson et al. |
| 6,845,269 | B2 | 1/2005 | Conley et al. |
| 6,847,842 | B1 | 1/2005 | Rodenhiser et al. |
| 6,873,875 | B1 | 3/2005 | Gilkerson et al. |
| 6,941,167 | B2 | 9/2005 | Stahmann et al. |
| 6,957,100 | B2 | 10/2005 | Vanderlinde et al. |
| 2002/0077562 | A1 | 6/2002 | Kalgren et al. |
| 2002/0077667 | A1 | 6/2002 | Gilkerson et al. |
| 2002/0077668 | A1 | 6/2002 | Kalgren et al. |
| 2002/0077669 | A1 | 6/2002 | Lindh et al. |
| 2002/0077859 | A1 * | 6/2002 | Stahmann et al. ............... 705/3 |
| 2002/0082509 | A1 | 6/2002 | Vanderlinde et al. |
| 2002/0082652 | A1 | 6/2002 | Wentkowski et al. |
| 2002/0082653 | A1 | 6/2002 | Stahmann et al. |
| 2002/0082657 | A1 | 6/2002 | Stahmann et al. |
| 2002/0082663 | A1 | 6/2002 | Stahmann et al. |
| 2002/0107552 | A1 | 8/2002 | Krig et al. |
| 2002/0120311 | A1 | 8/2002 | Lindh et al. |
| 2002/0123768 | A1 | 9/2002 | Gilkerson et al. |
| 2002/0156389 | A1 | 10/2002 | Kalgren et al. |
| 2002/0177881 | A1 | 11/2002 | Conley et al. |
| 2003/0004550 | A1 | 1/2003 | Stahmann et al. |
| 2003/0088291 | A1 | 5/2003 | Anderson et al. |
| 2003/0088292 | A1 | 5/2003 | Anderson et al. |
| 2003/0093123 | A1 | 5/2003 | Stahmann et al. |
| 2003/0105491 | A1 | 6/2003 | Gilkerson et al. |
| 2003/0187365 | A1 | 10/2003 | Eberle et al. |
| 2003/0199931 | A1 | 10/2003 | Stahmann et al. |
| 2004/0082976 | A1 | 4/2004 | Kalgren et al. |
| 2004/0111131 | A1 | 6/2004 | Hu et al. |
| 2004/0143305 | A1 | 7/2004 | Kalgren et al. |
| 2004/0230232 | A1 | 11/2004 | Gilkerson et al. |
| 2004/0243188 | A1 | 12/2004 | Vanderlinde et al. |
| 2004/0243194 | A1 | 12/2004 | Gilkerson |
| 2005/0010258 | A1 | 1/2005 | Peterson et al. |
| 2005/0021099 | A1 | 1/2005 | Stahmann et al. |
| 2005/0033385 | A1 | 2/2005 | Peterson et al. |
| 2005/0096708 | A1 | 5/2005 | Seim et al. |
| 2005/0187588 | A1 | 8/2005 | Stahmann et al. |
| 2005/0256550 | A1 | 11/2005 | Gilkerson et al. |

FOREIGN PATENT DOCUMENTS

| | | |
|---|---|---|
| EP | 0558353 A2 | 9/1993 |
| EP | 0565084 A2 | 10/1993 |
| EP | 0711531 A1 | 5/1996 |
| WO | WO-99/27992 A1 | 6/1999 |

OTHER PUBLICATIONS

Advisory Action mailed Feb. 13, 2004 in U.S. Appl. No. 09/738,868, 2 pgs.
Amendment and Response mailed Jan. 23, 2004 in U.S. Appl. No. 09/738,858, 16 pgs.
Amendment and Response mailed Oct. 15, 2003 in U.S. Appl. No. 09/738,868, 17 pgs.
Amendment and Response mailed Dec. 6, 2004 in U.S. Appl. No. 09/738,868, 19 pgs.
Amendment and Response mailed Jun. 9, 2004 in U.S. Appl. No. 09/738,868, 14 pgs.
Amendment and Response mailed Jul. 25, 2001 in U.S. Appl. No. 09/372,157, 13 pgs.
Final Office Action mailed Oct. 5, 2004 in U.S. Appl. No. 09/738,868, 6 pgs.
Final Office Action mailed Nov. 26, 2003 in U.S. Appl. No. 09/738,868, 7 pgs.
"French CNH Equipment Approvals", *Clinica*, 417, p. 9, (Sep. 5, 1990), 3 pgs.
Non-Final Office Action mailed Apr. 15, 2004 in U.S. Appl. No. 09/738,868, 7 pgs.
Non-Final Office Action mailed Apr. 25, 2001 in U.S. Appl. No. 09/372,157, 9 pgs.
Non-Final Office Action mailed Jul. 17, 2003 in U.S. Appl. No. 09/738,868, 10 pgs.
Notice of Allowance mailed Jan. 13, 2005 in U.S. Appl. No. 09/738,868, 7 pgs.
Notice of Allowance mailed Feb. 12, 2002 in U.S. Appl. No. 09/372,157, 5 pgs.
Notice of Allowance mailed May 12, 2001 in U.S. Appl. No. 09/676,318, 8 pgs.
Notice of Allowance mailed Sep. 6, 2002 in U.S. Appl. No. 09/569,928, 10 pgs.
Notice of Allowance mailed Sep. 7, 2001 in U.S. Appl. No. 09/372,157, 6 pgs.
"Pacemaker System Guide for PULSAR MAX II; Mulitprogrammable Pacemakers", Product brochure published by Guidant Corporation, (Apr. 18, 1999), pp. 6-48 and 6-49.
"Pacemaker System Guide for PULSAR MAX II; Multiprogrammable Pacemakers", Product brochure published by Guidant Corporation, (Apr. 18, 1999), pp. 6-39-6-51.
Preliminary Amendment mailed Sep. 29, 2000 in U.S. Appl. No. 09/676,318, 5 pgs.
"Rate-Adaptive Devices Impact Pacemaker Market", *Clinica*, 467, p. 16, (Sep. 11, 1991), 6 pages.
Request for Continued Examination mailed Dec. 7, 2001 in U.S. Appl. No. 09/372,157, 8 pgs.
Request for Continued Examination mailed Feb. 24, 2004 in U.S. Appl. No. 09/738,868, 3 pgs.
"Vitatron Medical Harmony™ Automatic Dual Chamber Pacemaker Product Information and Programming Guide", Product Brochure published by Vitatron Medical, (prior to May 6, 2004), 22 pgs.
Blommaert, D., et al., "Effective Prevention of Atrial Fibrillation by Continuous Atrial Overdrive Pacing After Coronary Artery Bypass Surgery", *Journal of the American College of Cardiology*, 35(6), (May 2000), 1411-1415.
Campbell, R. M., et al., "Atrial Overdrive Pacing for Conversion of Atrial Flutter in Children", *Pediatrics*, 75(4), (Apr. 1985), 730-736.
Fromer, M., et al., "Algorithm for the Prevention of Ventricular Tachycardia Onset: The Prevent Study", *The American Journal of Cardiology*, 83 (5B), (Mar. 11, 1999), pp. 45D-47D.
Garrigue, S., et al., "Prevention of Atrial Arrhythmias during DDD Pacing by Atrial Overdrive", *Pace*, vol. 21, (Sep. 1998), 1751-1759.
Heuer, H., et al., "Dynamische Zweikammer-Overdrive-Stimulation mit einem implantierbaren Schrittmachersystem als neue Methode zur Beendigung Langsamer ventrikularer Tachykardien", *Z Kardiol* 75. (English Abstract), (1986), 673-675.
Murgatroyd, F. D., et al., "A New Pacing Algorithm for Overdrive Suppression of Atrial Fibrillation", *Pace*, vol. 17., (Nov. 1994, Part), 1966-1973.
Sutton, R., "Pacing in Atrial Arrhythmias", *Pace*, vol. 13, (Dec. 1990, Part), pp. 1823-1827.
Zhu, D. W., "Electrophysiology, Pacing and Arrhythmia—Pacing Therapy for Atrial Tachyarrhythmias", *Clinical Cardiology*, 19(9), (1996), 737-742.

* cited by examiner

IMPLANTABLE MEDICAL DEVICE PROGRAMMING APPARATUS HAVING A GRAPHICAL USER INTERFACE

CROSS REFERENCE TO RELATED APPLICATION

This application claims priority from provisional application Ser. No. 60/468,902, filed May 7, 2003, and which is incorporated herein by reference.

TECHNICAL FIELD

The present device relates generally to implantable cardiovascular medical devices and particularly, but not by way of limitation, to systems for a configurable programmer for an implantable cardiovascular medical device, in which the programmer includes a graphical user interface to visualize programming processes and other data relating to the device, including medical data and device operation data.

BACKGROUND

When functioning properly, the human heart maintains its own intrinsic rhythm based on physiologically-generated electrical impulses. It is capable of pumping adequate blood throughout the body's circulatory system. Each complete cycle of drawing blood into the heart and expelling it is referred to as a cardiac cycle.

However, some people have abnormal cardiac rhythms, referred to as cardiac arrhythmias. Such arrhythmias result in diminished blood circulation. Arrhythmias can occur in the upper chambers of the heart—the atria, or the lower chambers of the heart—the ventricles. However, ventricular arrhythmias present the most serious health risk as they can lead to rapid death from the lack of circulation. Arrhythmias are further subdivided into specific conditions of the heart that represent vastly different manifestations of abnormal cardiac rhythm. These conditions are bradycardia, or a slow heartbeat, and tachycardia, or a fast heart beat. Fibrillation and flutter, which are essentially random and incoherent heart twitches where no pumping action is occurring at all, are potentially the most serious arrhythmias.

Increasingly, clinicians use implantable medical devices ("IMDs") to monitor and control arrhythmias. IMDs include pacemakers, also referred to as pacers, and defibrillators. A traditional use of a pacemaker is to treat bradycardia by stimulating cardiac rhythm. Pacers accomplish this by delivering timed sequences of low energy electrical stimuli, called pace pulses, to the heart. Such stimuli are delivered via an intravascular lead wire or catheter (referred to as a "lead") having one or more electrodes disposed in or about the heart.

In comparison to a pacemaker, an implanted defibrillator applies a much stronger electrical stimulus to the heart. This is sometimes referred to as a defibrillation countershock, also referred to simply as a "shock." The shock changes ventricular fibrillation to an organized ventricular rhythm or changes a very rapid and ineffective cardiac rhythm to a slower, more effective rhythm. Defibrillators help treat cardiac disorders that include ventricular fibrillation, ventricular tachycardia, atrial fibrillation, and atrial flutter. These inefficient or too rapid heartbeats reduce the pumping efficiency of the heart and thereby diminish blood circulation. The countershock delivered by the defibrillator interrupts the tachyarrhythmia, allowing the heart to re-establish a normal rhythm for the efficient pumping of blood.

Another mode of treating a cardiac arrhythmia uses drug therapy. Drugs are often effective at restoring normal heart rhythms. However, regardless of the method used to treat an arrhythmia, the therapeutic goal is to convert the irregular heartbeat into a normal or more regular pattern.

Modern IMDs can separately sense and coordinate the contractility of both the upper (atria) and lower (ventricles) chambers of the heart and serve as dual pacer/defibrillators. IMDs can further serve as a component of a comprehensive patient management system for predictive management of patients with chronic disease.

Presently, even the most basic IMDs typically have more than one arrhythmia detection criterion—tiered therapy which combines bradycardia support pacing with various antitachycardia pacing modes, low-energy cardioversion, defibrillation, and data logging capabilities. The data logging capabilities of IMDs have become increasingly important, since the amount of data required for the IMDs' operation increases proportionally with the increase in IMD functions. Efficiently processing this large amount of data has become possible with the incorporation of microprocessors and memory with the IMD.

Once an IMD has been implanted, the clinician interacts with the IMD through a clinical programmer. The clinical programmer is used to establish a telemetric link with the implanted IMD. The telemetric link allows for instructions to be sent to the electronic circuitry of the IMD and clinical data regarding the occurrence and treatment of a patient's cardiac arrhythmias and the IMDs operation to be sent from the electronic circuitry of the IMD to the programmer. The typical programmer is a microprocessor based unit that has a wand for creating the telemetric link between the implanted IMD and the programmer, and a graphics display screen that presents a patient's recorded cardiac data and IMD system information to the physician.

With implantable medical devices now capable of conducting sophisticated monitoring and treatment of cardiovascular disease, configuring the device has become increasingly critical to treatment efficacy and patient safety. A programmer allows the clinician to configure the device to meet these goals. In addition, because of rapid advances in computer technology, clinicians now have sophisticated programming tools capable of non-invasive programming and display of medical data in graphic and alpha-numeric forms.

As computer technology left the domain of esoteric scientific research and became accessible to non-computer experts for everyday use, alpha-numeric systems were typically the only way to program computer operation. Typically, a computer user would type a character string to program the computer to perform a specific function and then be limited to an alpha-numeric display of the computer's output.

As IMD feature sets become richer and more complex, IMDs are getting increasingly more complicated to program. This is especially the case in situations where modifications of one feature ripples through and interacts with other selected features.

For IMDs it can be very difficult for clinicians to deal with non-compatibilities with a programmer's features. Such devices may have many features to program and, when clinician attempts to program an IMD through a programmer, there may be some inconsistencies that are not allowed by logic or because of concerns for the patient's safety. In the past, these inconsistencies were displayed as error messages and the clinician often had to wade through a series of screens to determine the nature of the inconsistency and how to resolve it.

In addition, clinician were frustrated by error messages, which noted an interaction but did not tell the clinician what to do to resolve the problem. Clinicians were often reduced to trial and error programming which might create a second parameter interaction while resolving the first.

Programmers also have other limitations. Typically, IMD parameters were set by selecting from a list of possible options via the programmer. However, the options were often scattered throughout the programmer user interface.

However, as computer processing, memory and display systems improved, operating systems were developed that allowed the clinician to program an IMD by using a programmer with a graphical interface. In addition, clinicians could view computer output graphically. This gave clinicians greater control over computer functions and to recognize and analyze trends in computer output data more efficiently.

The first graphical user interface ("GUI") has been attributed to Xerox Corporation's Palo Alto Research Center in the 1970s, but it was not until the 1980s when graphical user interfaces became commercially feasible and popular. In addition to their visual components, graphical user interfaces used as medical tools make it easier to manipulate data in creative ways to gain different perspectives and a better understanding of the data's clinical significance.

For implantable medical devices, one way to manipulate the data perspective of the device is through the use of a programmer that employs a GUI. Programmer systems for implantable medical devices now use GUIs to graphically visualize the programming process and results. The obvious advantage of a GUI system over an alpha-numeric system is the ability to visually analyze the device's operation and the patient's medical data through the interface. In this way, the device is easier to use and configure, and provides the clinician with a better understanding of the therapies available to the patient and the data relative to the device. In sum, such a programmer allows the clinician to track and monitor the status of the IMD and the data it collects.

The use of graphics in the diagnosis and treatment of disease increases the clinician's ability to interface and understand the many parameters that can be changed to customize the device's therapy to the patient's specific needs and to analyze large amounts of medical data. Such graphics may include line graphs, bar charts, pie charts, dialog boxes, meters, color charts, the use of color, analog and digital representations, icons, symbols, buttons, etc.

One such GUI-based programmer is the ZOOM™ programming system by Guidant. It employs a GUI that improves the speed, precision and easibility of programming an implantable medical device and enables clinicians to make better decisions, faster. Thus, fast accurate decisions can be achieved with GUIs that improve the way graphical data is presented to the clinician and are configurable for more precise clinical evaluations or diagnoses.

However, a needed improvement is a more intuitive way for the physician to resolve parameter interactions and a user interface that allows related parameters to be displayed simultaneously to enhance the clinician's resolution of parameter interaction conflicts and the impact of programming on patient health. For example, GUIs should be capable of visualizing cardiovascular events, therapeutic interventions or device operation quickly and efficiently to focus a clinician's attention on potential problems. In addition, GUI-based programmers should assist the clinician in analyzing the large amount of patient data monitored and recorded by the device. In this way, the GUI-based programmer empowers the clinician to effectively manage patient therapy through the medical device. GUI-based programmers should also allow the clinician to analyze device operation within the context of physiological parameters like the anatomy of the heart. When testing or evaluating the implantable medical device's operation or function, a GUI-based programmer should be capable of visually guiding the clinician through the steps of the process so the clinician is fully aware of what is taking place and when. In addition, a GUI-based programmer should have a graphically-based safety feature that prevents a clinician from making an inadvertent and potentially dangerous change to the device's operating parameters.

Thus, for these and other reasons, there is a need for a GUI-based programmer for an implantable medical device that improves the tasks of: (1) alerting the clinician to potential problems with the patient's condition or the therapy provided by the device or the device itself; (2) efficiently and effectively managing patient therapy; and (3) efficiently and effectively managing device operation without compromising patient safety.

SUMMARY

According to one aspect of the invention, there is provided a system for a implantable medical device programmer that employs a graphical user interface for programming the device and monitoring and analyzing patient data. As used herein, "patient data," "patient health data," "medical information" and "biometric data" are substantively synonymous terms, as are the words "data" and "information." These terms include the patient data sensed, monitored and recorded by the implantable medical device and/or the data reported by the device. Also, as used herein, a "clinician" can be a physician, physician assistant (PA), nurse, medical technologist, or any other patient health care provider.

The implantable medical device programmer with a graphical user interface is a component of a cardiovascular disease treatment system comprising an implantable medical device with a power supply, a communications component typically comprising a telemetric wand—the wand being in electronic communication with a programmer. The programmer further comprises an input component and a display component. The GUI of the present invention interfaces within both input and display components.

In one embodiment, the GUI comprises a configurable alert for action. The alert allows the user or clinician to easily identify important diagnostic or therapeutic events, changes or device settings by means of colors and/or symbols.

In another embodiment, the GUI comprises graphical displays of patient data sensed by the medical device. The graphical displays may include pie charts of counted arrhythmic events, such as bradycardic or tachycardic events.

In a further embodiment, the GUI comprises graphical displays of the operation of the medical device, such as a test of a device lead. Such displays may be organized according to the anatomical position of the lead, i.e., whether the lead is an atrial or ventricular lead. This allows the clinician to efficiently assess the functionality of all lead data by virtue of its grouping into precise anatomical categories.

In yet another embodiment, the GUI comprises a moving graphical indicator that quickly identifies the type and duration of any specific functional test of the medical device. This moving graphical indicator enhances the clinician's perception of control over the functional test process and focuses the clinician's attention on the specific information generated by the test.

In yet a further embodiment, the GUI comprises a one-click on/off feature to manage the atrial arrhythmia management features of the implantable medical device. This feature allows the clinician to take greater advantage of an implantable medical device's powerful atrial arrhythmia management features.

In another embodiment, the GUI comprises a display that summarizes programming changes to the implantable medical device to let a clinician review any proposed changes to the programming of the implantable medical device before they are downloaded to the device. In this way, the GUI provides an additional safety feature by displaying all the proposed programming changes to the implantable medical device before they are transmitted to the device, even those changes made automatically by the device in response to a purposeful change by the clinician. This feature reduces the risk of adversely affecting the device's efficacy or harming the patient.

In yet another embodiment, the GUI comprises a feature that allows the clinician to focus on a specific time interval and view all the clinical and therapeutic events that took place during that interval, including any notes the clinician might have entered into the programmer's graphical interface relative to an event.

These and various other features, as well as advantages, which characterize the present invention, will be apparent from a reading of the following detailed description and a review of the drawings.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DESCRIPTION OF THE PREFERRED EMBODIMENT

In the following detailed description, reference is made to the accompanying drawings that form a part hereof, and in which are shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The present system is described with respect to an implantable medical device programmer that uses a graphical user interface to program the device and monitor and analyze patient data. Thus, the clinician can exert not only fine-tune control over the device's functionality, but also easily and efficiently monitor patient health status and adjust patient therapy accordingly. The system can also be integrated with an "Advanced Patient Management" system. The term "patient management" refers to the process of creating and collecting patient specific information, storing and collating the information, and generating actionable recommendations to enable the predictive management of patients with chronic disease.

Figure 1:
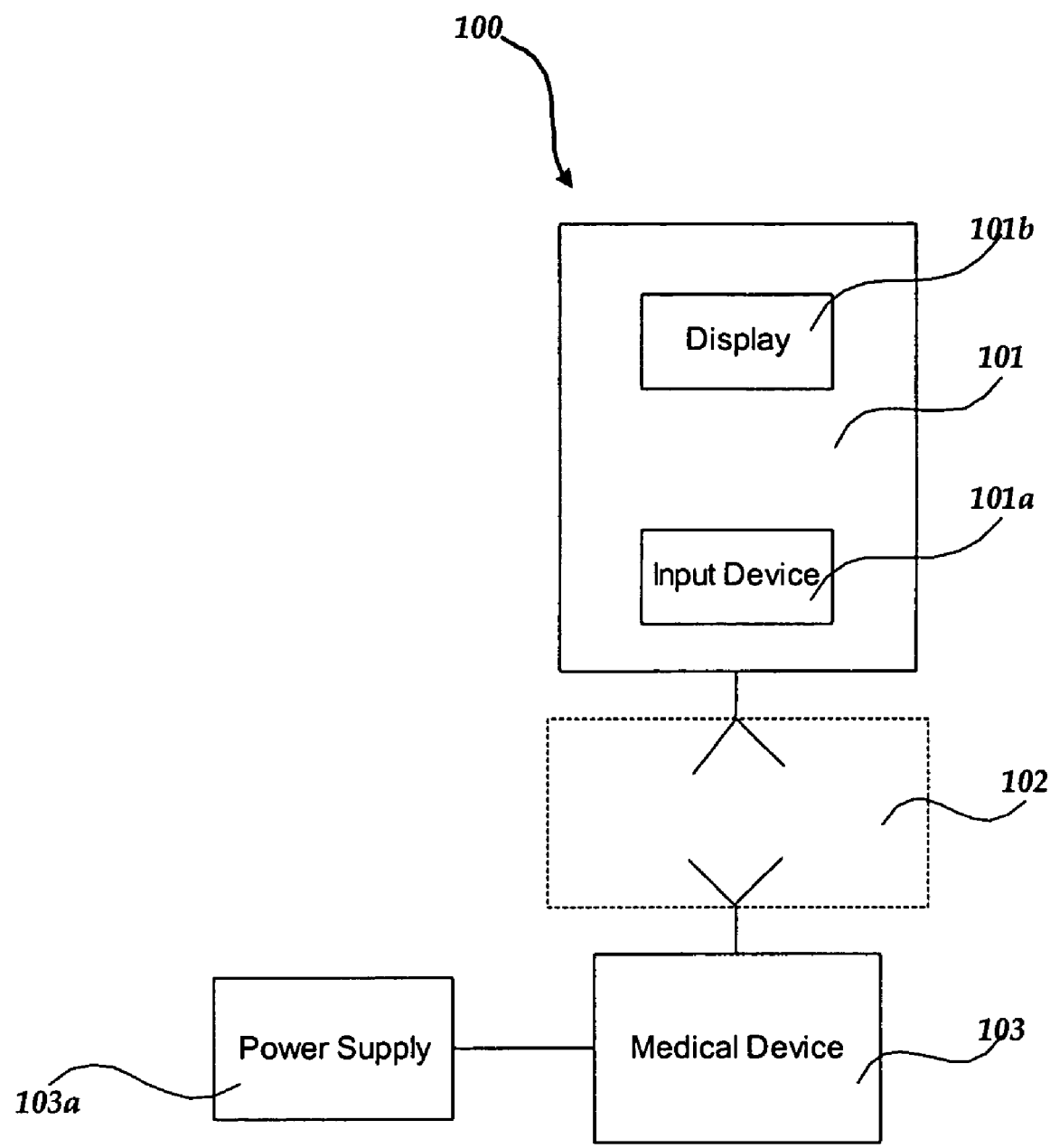
FIG. 1 is a schematic/block diagram illustrating generally, among other things, the components of a cardiovascular disease treatment system comprising a programmer, a communications component and a powered implantable medical device.

FIG. 1 is a schematic/block diagram illustrating generally, among other things, the components of a cardiovascular disease treatment system 100 comprising a programmer 101, a communications component 102 and a powered implantable medical device. The programmer comprises an input component 101*a* and a GUI accessible through a display component 102*b*. The features of the GUI can be accessed by any means known in the art such as by keyboard, touch or stylus. The GUIs of the present invention may interface with both input 101*a* and display 101*b* components. The communications component 102 may comprise a telemetric wand that wirelessly transmits data between the programmer and the implantable medical device. The implantable medical device 103 may comprise a pacer, a defibrillator or a combination device that performs both functions. Regardless of the configuration, the implantable medical device further comprises an internal power supply 103*a*, typically a long-life battery, like a lithium-based or other battery. The system may comprise a component of a more comprehensive patient management system designed to integrate all aspects of a patient's treatment into a coherent system.

Figure 2:
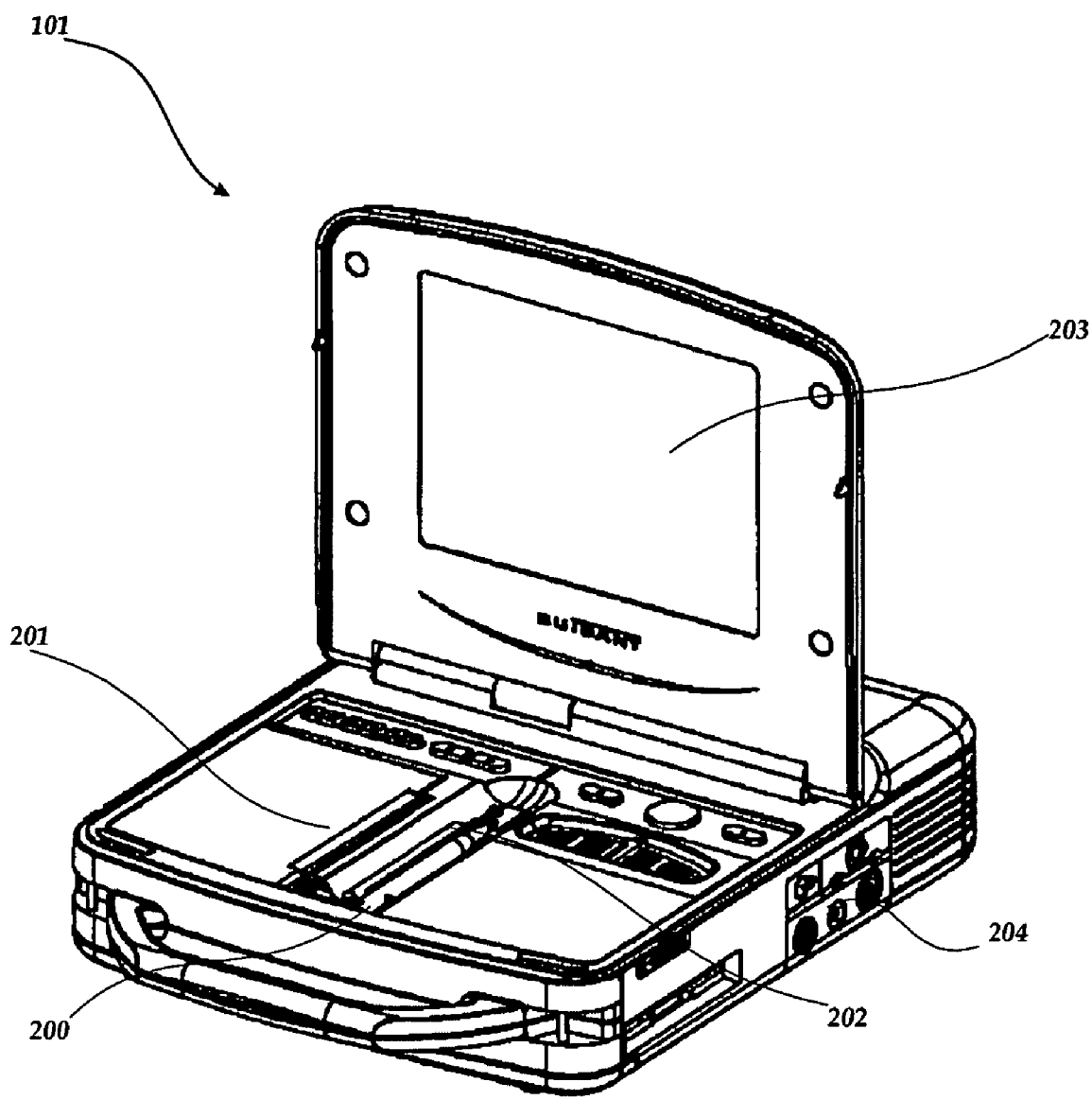
FIG. 2 is a diagram illustrating generally, among other things, an implantable medical device programmer comprising a GUI.

FIG. 2 is a diagram illustrating generally, among other things, an implantable medical device programmer comprising a GUI 101. In this embodiment, the programmer 101 comprises a telemetry wand 200, a strip-chart printer 201, a touchscreen stylus 202 and a display screen 203 to display the GUI. The telemetry wand is adapted to electronically interrogate an implantable medical device, thus allowing the programmer 101 to wirelessly receive and transmit medical and programming data. The programmer 101 also comprises a display screen or monitor 203 adapted to display the GUI with adequate resolution and color quality. Typically, a display screen capable of displaying an electrocardiogram (ECG) is sufficient. The programmer is portable and further comprises ports 204 optional external devices like a VGA monitor or a printer.

Figure 3:
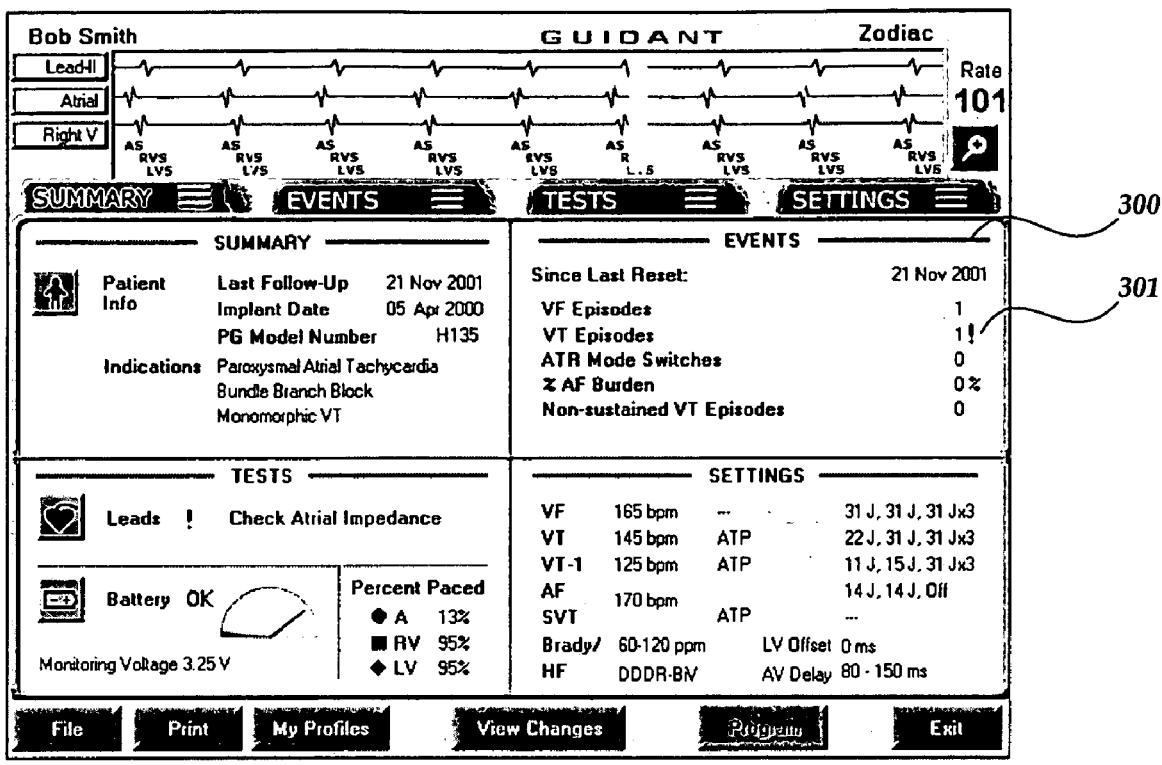
FIG. 3 is a screen shot of a GUI illustrating generally, among other things, an alert relating to a cardiovascular event.

FIG. 3 is a screen shot of a GUI illustrating generally, among other things, an alert relating to a cardiovascular event 300. In this embodiment, the invention uses colors and symbols to denote arrhythmias that require a clinician's attention more so than other arrhythmias. The specific arrhythmias could include an accelerated episode or an episode requiring multiple therapies to convert. A color and symbol can denote an actionable alert. By way of non-limiting example only, the color may comprise red and the symbol may comprise an exclamation point. The GUIs of the present invention are not only adapted to alert a clinician to a past episode, but also can flag specific episodes for a clinician to look at more carefully. By using colors and symbols in this way, the clinician can further prioritize the event and device settings that need the most attention. This allows the clinician to quickly and easily identify an event and alter the therapy to prevent a recurrence of the event. The information shown in this figure represents a summary of the more detailed information shown in FIG. 4 below.

Figure 4:
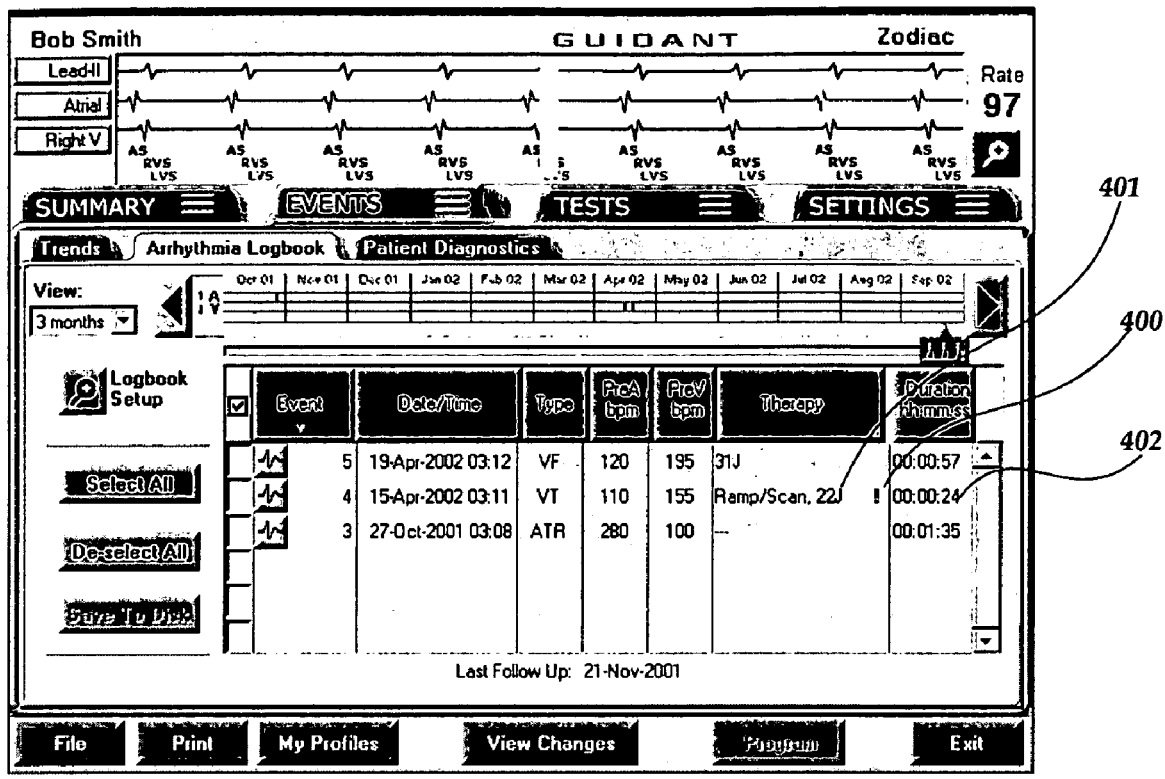
FIG. 4 is a screen shot of a GUI illustrating generally, among other things, an alert relating to a therapeutic event.

FIG. 4 is a screen shot of a GUI illustrating generally, among other things, an alert relating to a therapeutic event. In this embodiment, the GUI not only alerts the clinician to an important clinical event 400, like the single ventricular tachycardia episode as shown in FIG. 3, but also to the therapeutic event of interest 401 associated with the clinical event 400. As shown in FIG. 4 by way of non-limiting example only, such a therapeutic event 400 may comprise the extent of the therapy needed to correct the tachycardia 401 402.

Figure 5:
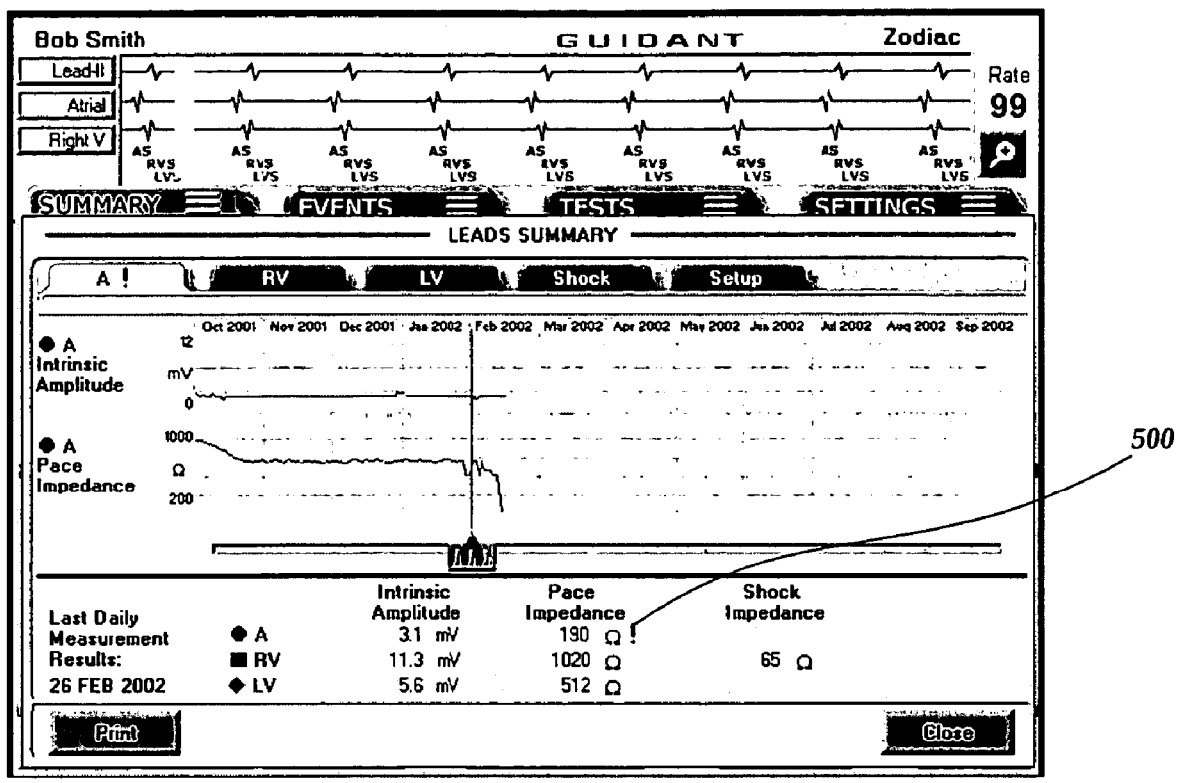
FIG. 5 is a screen shot of a GUI illustrating generally, among other things, an alert relating to a device event.

FIG. 5 is a screen shot of a GUI illustrating generally, among other things, an alert relating to a device event 500. In this embodiment, the GUI flags problems with the device itself or one of its components, like a lead. As shown in FIG. 4, the pace impedance of the atrial lead is outside expected parameters and may require the clinician's attention. Flagging a device problem in this fashion allows a clinician to easily identify and correct problems with the device.

Figure 6:
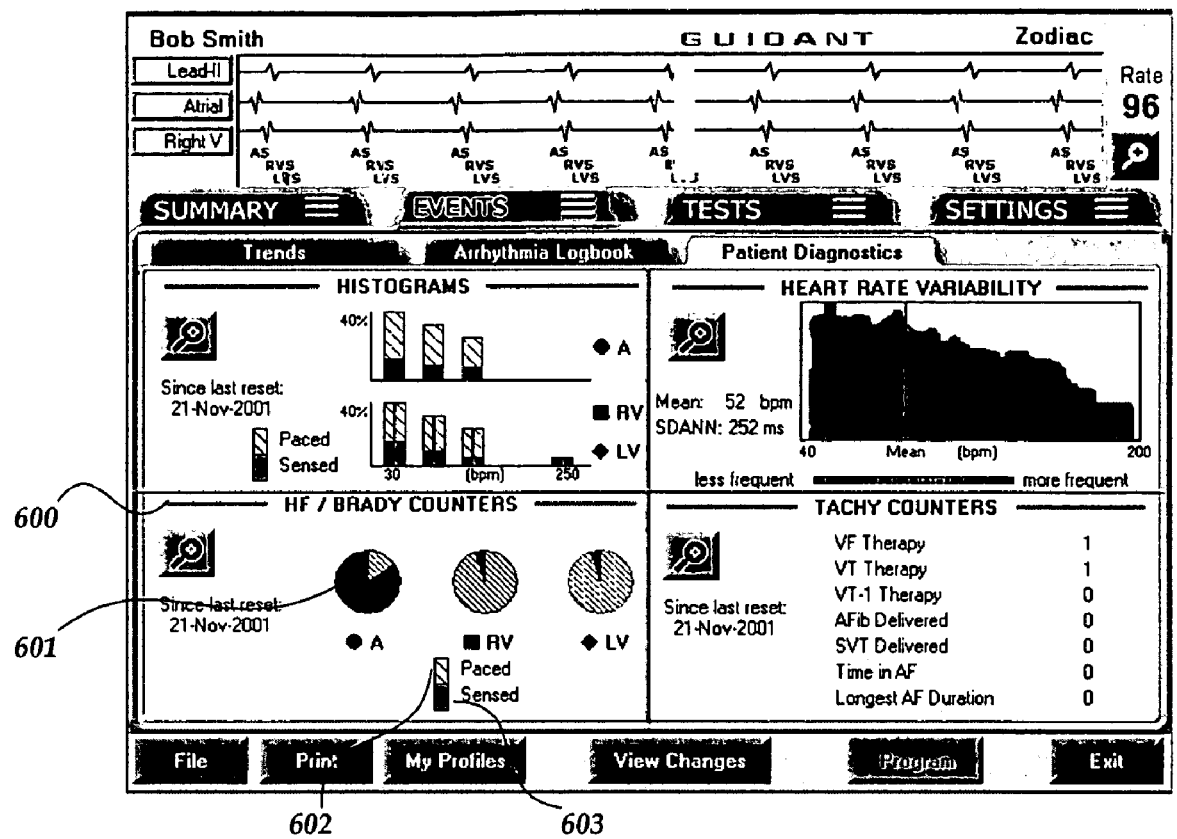
FIG. 6 is a screen shot of a GUI illustrating generally, among other things, a graphical display of a counted cardiovascular event.

FIG. 6 is a screen shot of a GUI illustrating generally, among other things, a graphical display of a counted cardiovascular event. Implantable medical devices are often configured to keep a record of, or count, significant cardiovascular events. Such an event may include the number of bradycardia episodes 600 experienced by a patient. Typically, bar charts are used to visualize this information. However, it is often not clear from a bar chart the frequency of a cardiovascular event. Pie charts 601 can help solve this problem. As shown in FIG. 6, it is easier to analyze the percentage of bradycardia events in each heart chamber by reference to the pie charts 601. Of course, under different therapeutic regimens, the pie charts 601 may reflect different data. For example, the patient with a diseased sinoatrial node may reveal a pie chart with 100% pacing and 0% sensing of the atria and 0% pacing and 100% sensing of the ventricles. Thus, a graphic in the form of a pie chart 601 allows the clinician to easily see the relationship between pacing 602 and sensing 603 parameter values.

Figure 7:
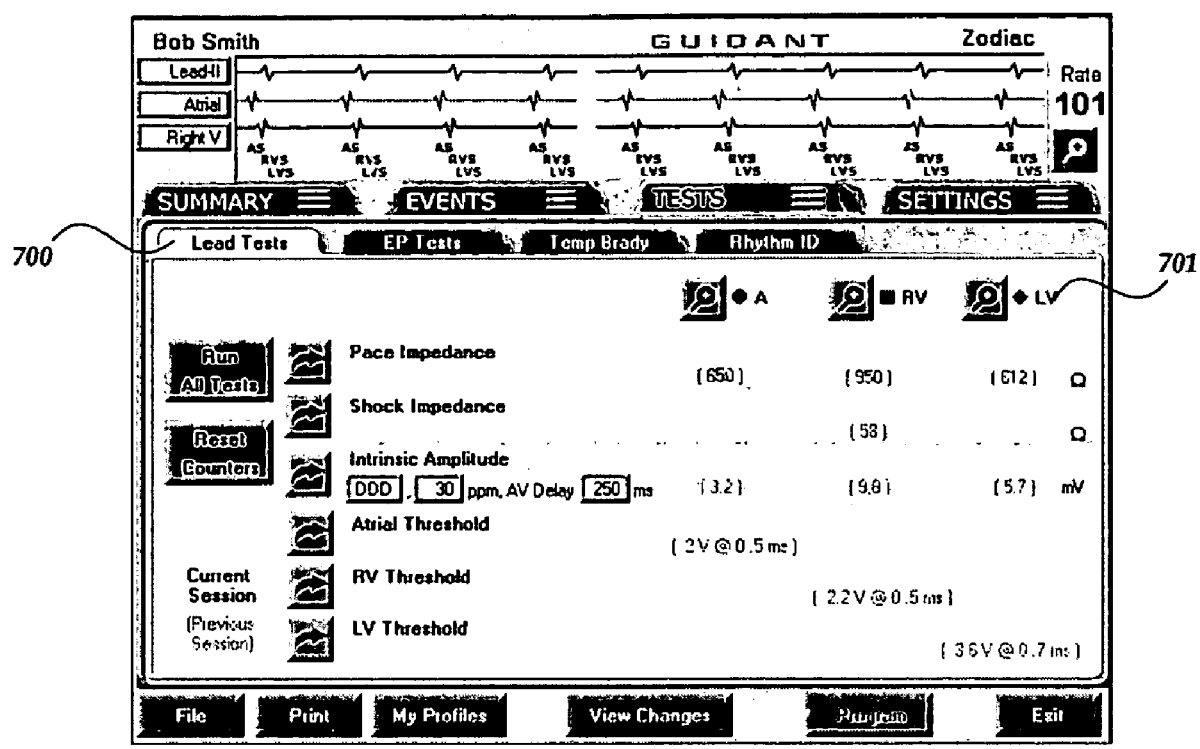
FIG. 7 is a screen shot of a GUI illustrating generally, among other things, a graphical display of a lead test grouped by heart chamber.

FIG. 7 is a screen shot of a GUI illustrating generally, among other things, a graphical display of a lead test 700 grouped by heart chamber. In this embodiment, the implantable lead tests and daily measurement data are grouped by chamber 701 rather than grouped by test type. This allows the clinician to easily view parameter values by chamber grouping, which further allows for a more efficient diagnostic of the device because all the lead data for a particular chamber is grouped on one screen.

Figure 8:
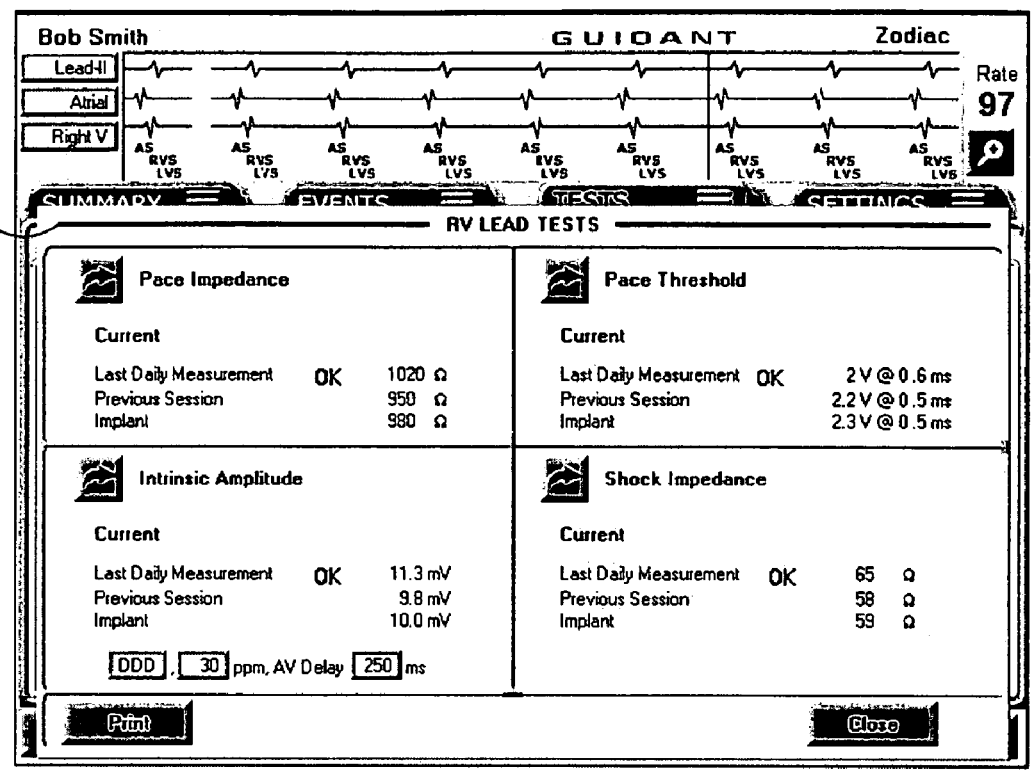
FIG. 8 is a screen shot of a GUI illustrating generally, among other things, another graphical display of a lead test grouped by heart chamber.

FIG. 8 is a screen shot of a GUI illustrating generally, among other things, another graphical display of a lead test 800 grouped by heart chamber. In this embodiment, lead test data as organized by each individual heart chamber. This figure shows the status of the leads in the right ventricle.

Figure 9:
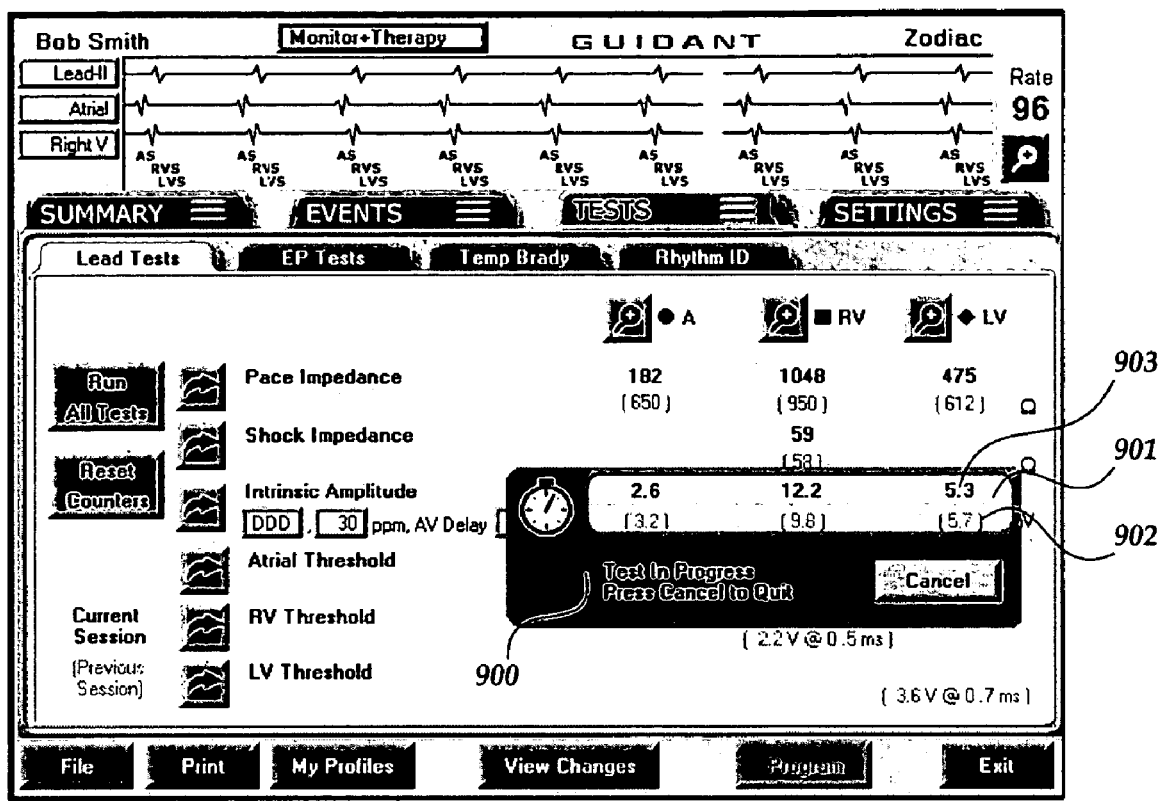
FIG. 9 is a screen shot of a GUI illustrating generally, among other things, a graphical display of a moving indicator reflecting a lead test operation.

FIG. 9 is a screen shot of a GUI illustrating generally, among other things, a graphical display of a moving indicator 900 reflecting a lead test operation. In this embodiment, the moving graphical indicator draws the clinician's attention to the functional test being performed. As the communications component 102 reports the test data to the input device, the graphical indicator shows the test results 901 and then moves to the next test when the preceding test is complete. This helps maintain the clinician's focus on which test is being performed at any given time as well as allowing the clinician to view previous 902 and current test 903 values.

Figure 10:
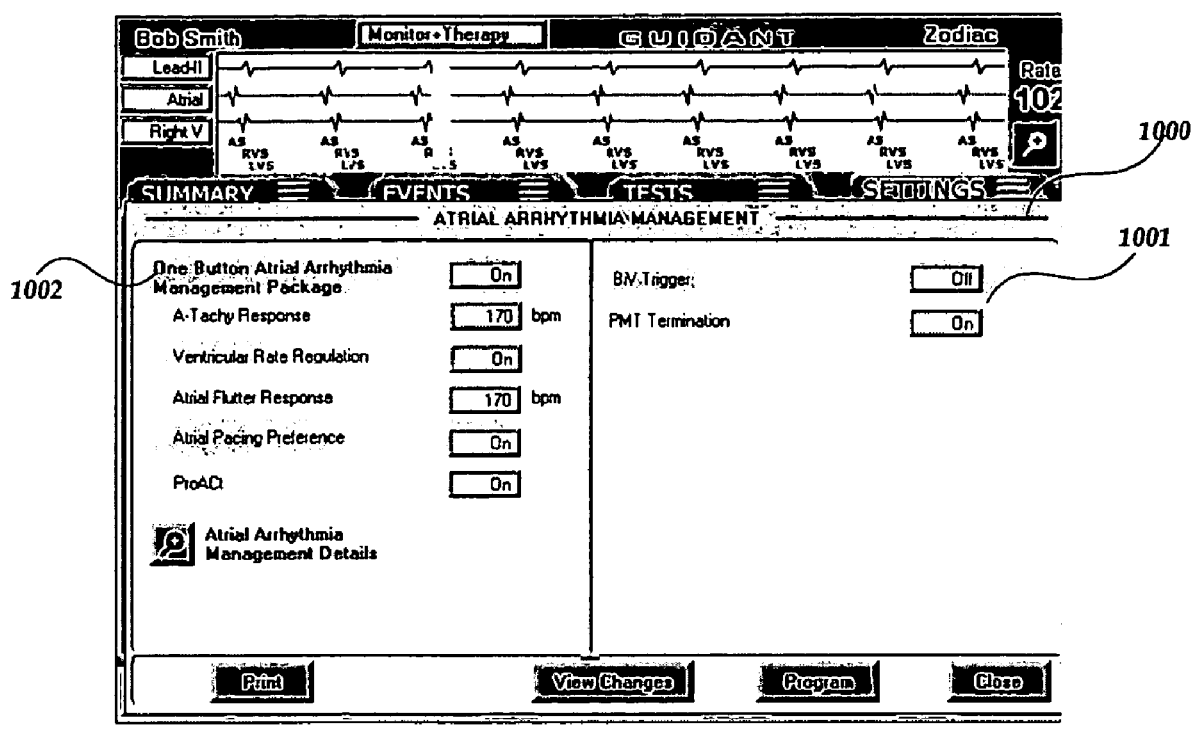
FIG. 10 is a screen shot of a GUI illustrating generally, among other things, a graphical display of an atrial arrhythmia management screen.

FIG. 10 is a screen shot of a GUI illustrating generally, among other things, a graphical display of an atrial arrhythmia management screen 1000. In this embodiment, the GUI comprises a one-click On/Off feature 1002 for a suite of atrial arrhythmia management features 1001. Thus, with the ease of clicking an icon on the display screen, the clinician has complete access to the programmers' powerful atrial arrhythmia management features. In addition, the clinician does not have to worry about setting up or activating each atrial management feature 1001 individually (i.e., A-Tachy Response, A-Flutter Response, A-Pacing Preference, etc.) because the one-touch feature 1002 when activated or deactivated sets all parameters appropriately.

Figure 11:
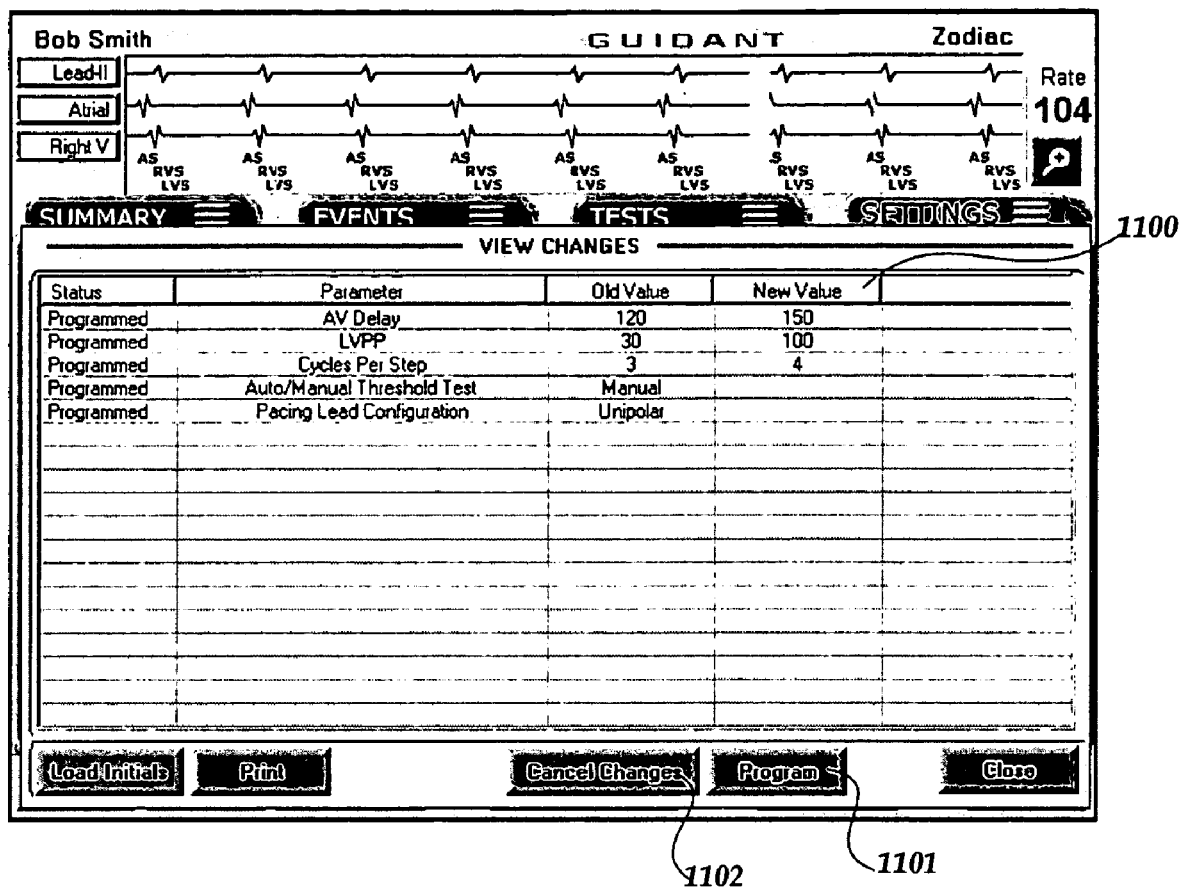
FIG. 11 is a screen shot of a GUI illustrating generally, among other things, a graphical display of proposed changes made to the programming of an implantable medical device before the changes are implemented.

FIG. 11 is a screen shot of a GUI illustrating generally, among other things, a graphical display of proposed changes 1100 to the programming of an implantable medical device before the changes are implemented. In this embodiment, the GUI provides the clinician with a summary of all proposed parameter changes 1100 for a medical device before the device is actually programmed 1101 with those changes. This allows the clinician a final opportunity to review and make corrections 1102. In addition, this embodiment comprises the option to require the clinician to first view the proposed programming changes before they are implemented. This is in stark contrast to prior art systems that allow the clinician to view programming changes to an implantable medical device as merely an option before implementing the changes. Because this embodiment removes that option, it provides an additional layer of safety that reduces the risks to the patient due to improper changes to the device's programming.

Figure 12:
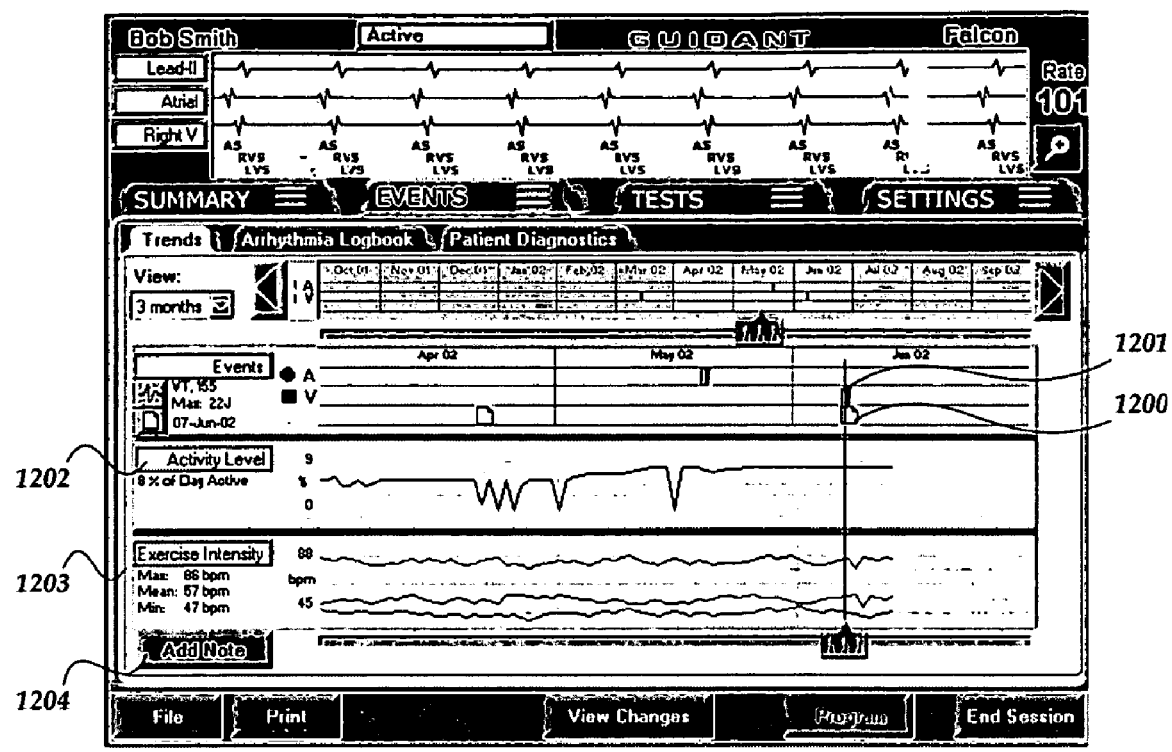
FIG. 12 is a screen shot of a GUI illustrating generally, among other things, a graphical display of a time interval of clinical and therapeutic events comprising notes entered into the graphical interface.
Figure 13:
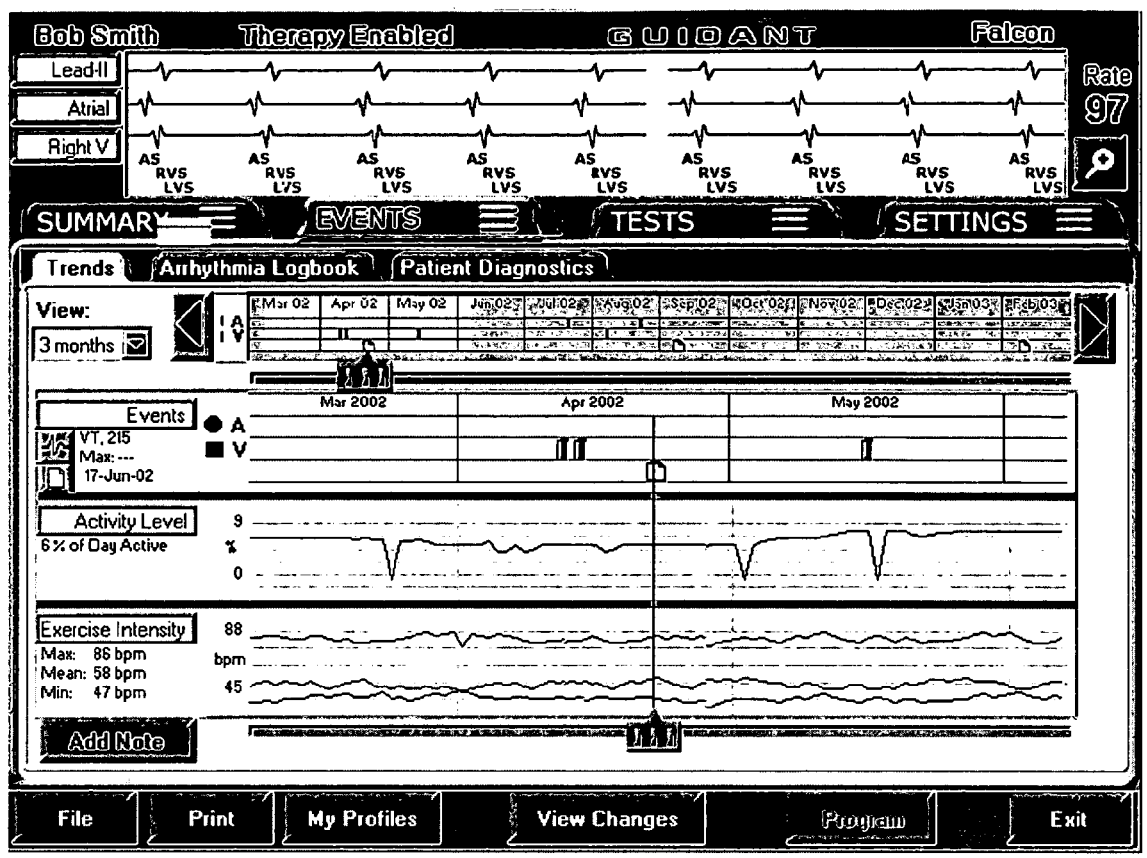
FIG. 13 is a screen shot of a GUI illustrating generally, among other things, another graphical display of a time interval of clinical and therapeutic events comprising notes entered into the graphical interface.

FIG. 12 is a screen shot of a GUI illustrating generally, among other things, a graphical display of a time interval of clinical and therapeutic events comprising notes 1200 entered into the graphical interface. The note can be relative to an event 1201 or not. In this embodiment, the GUI not only provides the clinician with a time interval view of clinical and therapeutic events, but it also shows certain wellness indicators during this period like Activity Level 1202 and Exercise Intensity 1203. As further shown in FIG. 12, the time interval is 3 months (April-June). This embodiment shows that within this period, an atrial and a ventricular event was recorded. In addition, the clinician made two notes within this period— one in April and one in June. The June note relates to a ventricular event. By selecting the note icon 1200 on the GUI, the clinician can review or revise the note. By selecting the "Add Note" button 1204, the clinician can add a new note. In this way, the GUI can record additional diagnostic, therapeutic or other information beyond that which may be normally captured and recorded by the programmer and/or the IMD. FIG. 13 is another embodiment of the concept illustrated in FIG. 12.

Figure 14:
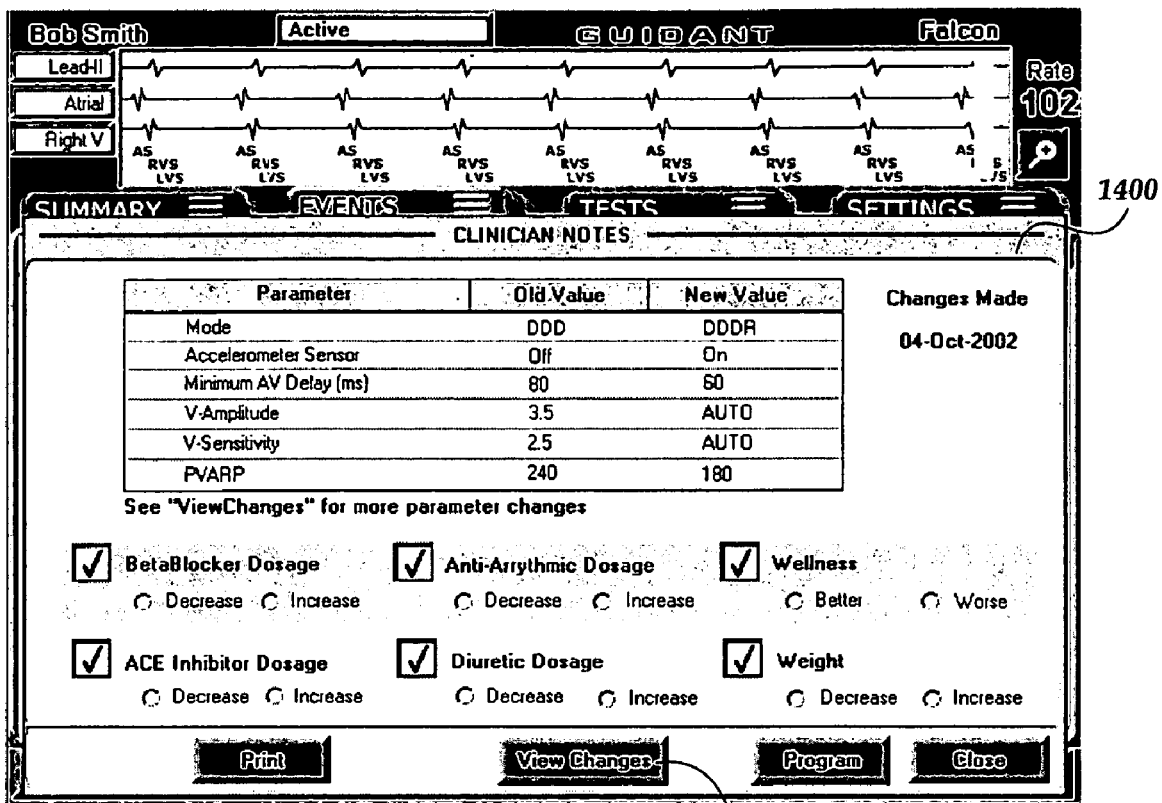
FIG. 14 is a screen shot of a GUI illustrating generally, among other things, a graphical display of the contents of a clinician's note.
Figure 15:
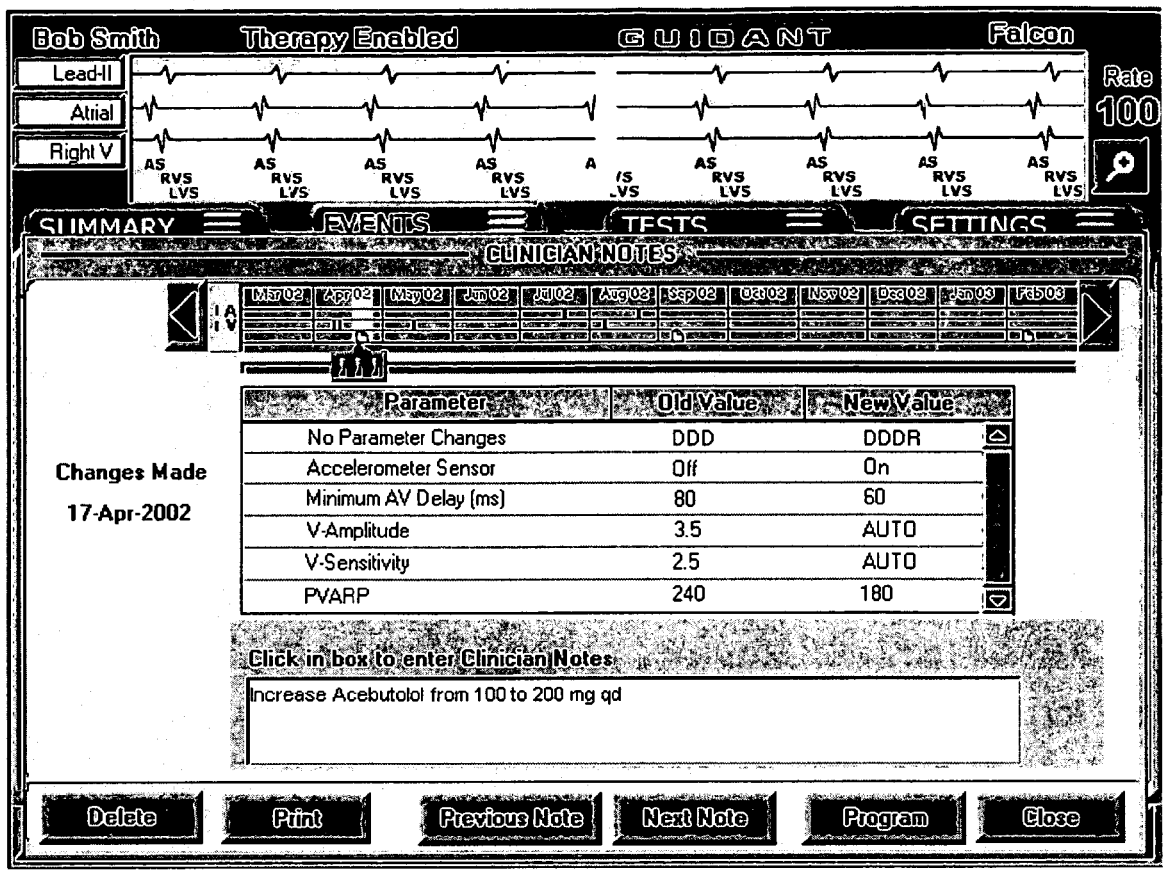
FIG. 15 is a screen shot of a GUI illustrating generally, among other things, another graphical display of the contents of a clinician's note.

FIG. 14 is a screen shot of a GUI illustrating generally, among other things, a graphical display of the contents 1400 of a clinician's note. In this embodiment, the clinician has selected a note icon and is able to view a record of the programming changes made to the device. The clinician in this embodiment can also view more parameter changes by selecting the "View Changes" button 1401. FIG. 15 is another embodiment of the concept illustrated in FIG. 14.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A system comprising:
an external programmer adapted to interface with an implantable medical device, the programmer comprising:
a communication module adapted to communicate with the implantable medical device; and
a graphical user interface adapted to communicate information to a user, the graphical user interface adapted to display a management screen configured to receive proposed programming changes initiated by a clinician, the clinician-initiated proposed programming changes including a suite of parameters including A-Tachy Response, A-Flutter Response, Ventricular Rate Regulation, ProACt, and A-Pacing Preference, the management screen including a one-touch feature configured to set all parameters in the suite with actuation of the one-touch feature, and the graphical user interface further adapted to display, in response to and after all clinician-initiated proposed changes have been received in the management screen from the clinician, in a proposed changes screen different from the management screen, a summary of the clinician-initiated proposed changes to the programming of the implantable medical device, the clinician-initiated proposed changes shown on the proposed changes screen in visual correspondence with corresponding previously-existing parameter values, the proposed changes screen configured to require clinician review of the clinician-initiated proposed new parameter values and to allow clinician correction of the clinician-initiated proposed new parameter values before the clinician-initiated proposed new parameter values are implemented.

2. The system of claim 1, wherein the graphical user interface is adapted to display over time one or more patient clinical or therapy events, the display over time capable of including at least one user-editable note.

3. The system of claim 2, wherein the graphical user interface is adapted to display a time interval of one or more clinical events and one or more therapeutic events and one or more notes entered into the graphical user interface.

4. The system of claim 2, wherein the display over time includes a clinician's note associated with a particular time along with a listing of one or more implantable medical device parameters in effect at that particular time.

5. The system of claim 1, wherein the system further comprises the implantable medical device.

6. The system of claim 1, wherein the graphical user interface is also adapted to display a graphic alert displayed in visual correspondence with time relating to an arrhythmia episode.

7. The system of claim 1, wherein the graphical user interface is also adapted to display a graphic alert relating to an antitachyarrhythmia therapeutic event displayed in visual correspondence with a logged tachyarrhythmia episode.

8. The system of claim 1, wherein the graphical user interface is also adapted to display a graphic alert relating to a device lead test event.

9. The system of claim 1, wherein the graphical user interface is also adapted to display a graphical indication of a counted cardiovascular event.

10. The system of claim 1, wherein the graphical user interface is also adapted to display information about a lead test grouped by heart chamber.

11. The system of claim 1, wherein the graphical user interface is also adapted to display a visually moving indicator reflecting a lead test in operation.

12. The system of claim 1, in which the external programmer is adapted to automatically create a note documenting a change in parameter values in response to implementation of the clinician-initiated proposed new parameter values.

13. The system of claim 1, in which the graphical user interface is adapted to display an indication of a number of arrhythmic events of a particular type relative to a total number of events of the particular type.

14. The system of claim 1, in which the graphical user interface is adapted to display one or more pie charts indicating the number of arrhythmic events of the particular type relative to the total number of events of the particular type.

15. The system of claim 14, in which the one or more pie charts indicate the number of paced bradyarrhythmic events relative to the total number of paced and sensed events.

16. The system of claim 14, in which the one or more pie charts include:
a first pie chart separately indicating right ventricular paced events and right ventricular sensed events; and
a second pie chart separately indicating left ventricular paced events and left ventricular sensed events.

17. The system of claim 16, in which the one or more pie charts include a third pie chart separately indicating atrial paced events and atrial sensed events.

18. The system of claim 1, in which the graphical user interface is adapted to display:
a percentage of atrial beats that are paced beats;
a percentage of right ventricular beats that are paced beats; and
a percentage of left ventricular beats that are paced beats.

19. The system of claim 1, in which the graphical user interface is adapted to display an arrhythmia log that permits logging of multiple arrhythmia episodes along with a classification of each such arrhythmia episode by the implantable medical device and an indication of a responsive therapy, if any, that was delivered by the implantable medical device in response to the particular arrhythmia.

20. The system of claim 1, in which the graphical user interface is adapted to display a lead impedance value in visual correspondence with a graphic alert if the lead impedance value falls outside of an acceptable range.

21. A method comprising:

obtaining in a management screen of a graphical user interface proposed programming changes of an implantable medical device from a clinician using an external programmer, the clinician-initiated proposed programming changes including a suite of parameters including A-Tachy Response, A-Flutter Response, Ventricular Rate Regulation, ProACt, and A-Pacing Preference, the management screen including a one-touch feature configured to set all parameters in the suite with actuation of the one-touch feature;

displaying on the graphical user interface in a proposed changes screen different from the management screen, in response to the proposed programming changes initiated by the clinician and after all proposed programming is complete, a summary of the clinician-initiated proposed changes to the programming of the implantable medical device, the clinician-initiated proposed changes shown on the proposed changes screen in visual correspondence with corresponding previously-existing parameter values; and requiring clinician review of the proposed new clinician-initiated proposed parameter values and allowing clinician correction of the proposed new clinician-initiated proposed parameter values before the clinician-initiated proposed new parameter values are implemented.

22. The method of claim 21, further comprising displaying at least one user-editable note.

* * * * *